United States Patent [19]

Cantatore et al.

[11] Patent Number: 4,855,434
[45] Date of Patent: Aug. 8, 1989

[54] PIPERIDINE COMPOUNDS

[75] Inventors: Giuseppe Cantatore, Bitonto; Valerio Borzatta, Bologna, both of Italy

[73] Assignee: Ciba-Geigy Corporation, Ardsley, N.Y.

[21] Appl. No.: 156,112

[22] Filed: Feb. 16, 1988

[30] Foreign Application Priority Data

Feb. 26, 1987 [IT] Italy .................... 19500 A/87

[51] Int. Cl.[4] ............... C07D 401/12; C07D 401/14; C08K 5/34
[52] U.S. Cl. .......................... 546/190; 546/187; 524/99
[58] Field of Search .................. 546/187, 190

[56] References Cited

U.S. PATENT DOCUMENTS 4,140,673  2/1979  Lachmann et al. ............ 546/186

FOREIGN PATENT DOCUMENTS 3412227  10/1984  Fed. Rep. of Germany ...... 546/188

Primary Examiner—Robert T. Bond
Attorney, Agent, or Firm—Harry Falber

[57] ABSTRACT

The novel compounds of the formula (I)

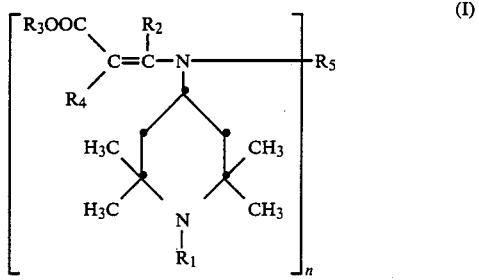

in which n is 1 or 2, $R_1$ is hydrogen, O·, NO, cyanomethyl, $C_1$–$C_8$-alkyl, $C_3$–$C_6$ alkenyl or $C_3$–$C_6$ alkynyl subject to the proviso that the carbon atom attached to the nitrogen atom is a primary carbon atom, benzyl, $C_1$–$C_7$ acyl or OH-monosubstituted $C_2$–$C_4$ alkyl, $R_2$ is hydrogen, $C_1$–$C_4$ alkyl or phenyl, $R_3$ is a group of the formula (II)

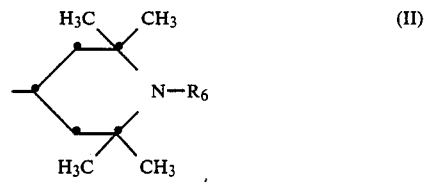

with $R_6$ being as defined for $R_1$, $R_4$ is —$COOR_3$ or —CN and, if n is 1, $R_5$ is hydrogen, $C_1$–$C_{18}$ alkyl, $C_2$–$C_4$ alkyl substituted by $C_1$–$C_{12}$ alkoxy or di($C_1$–$C_6$ alkyl)amino, or $C_5$–$C_{12}$ cycloalkyl unsubstituted or substituted by 1, 2 or 3 $C_1$–$C_4$ alkyl radicals, benzyl, benzyl substituted by 1,2 or 3 $C_1$–$C_4$ alkyl radicals, or a group of the formula (II), and, if n is 1 and $R_4$ is —CN, $R_3$ is additionally a group of the formula

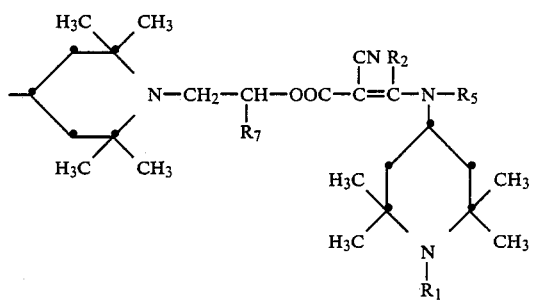

with $R_1$, $R_2$ and $R_5$ being as defined above and $R_7$ being as defined for $R_2$, and, if n is 2, $R_5$ is $C_2$–$C_{12}$ alkylene, $C_6$–$C_{15}$ cycloalkylene, phenylene, xylylene or $C_4$–$C_{12}$ alkylene which is interrupted in the chain by one or two oxygen atoms or one or two groups

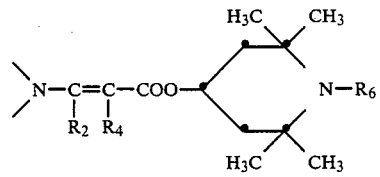

with $R_2$, $R_4$ and $R_6$ being as defined above, are useful for stabilizing organic material against oxidative, thermal and light-induced degradation.

8 Claims, No Drawings

PIPERIDINE COMPOUNDS

The present invention relates to novel piperidine compounds, the use thereof and to the organic material stabilized with the aid of said compounds against thermal, oxidative and light-induced degradation.

It is known that synthetic polymers and copolymers undergo progressive changes in their physical properties, such as loss of mechanical strength and colour changes, when they are exposed to sunlight or other sources of ultraviolet light.

To retard the deleterious effect of ultraviolet radiation on synthetic polymers and copolymers, it has been proposed to use various additives having light-stabilizing properties, such as certain derivatives of benzophenone and benzotriazole, nickel complexes, substituted benzoic acid esters, alkylidenemalonates, cyanoacrylates, aromatic oxamides and sterically hindered amines.

U.S. Pat. No. 4,140,673 and DE No. 34 12 227 describes piperidyl acrylates and their light stabilizing activity for synthetic polymers.

The present invention relates to novel compounds of the formula (I)

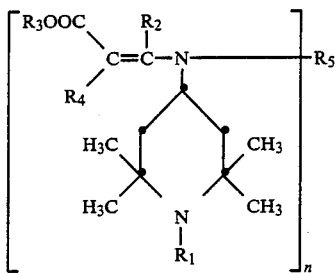

in which n is 1 or 2, $R_1$ is hydrogen, O°, NO, cyanomethyl, $C_1$-$C_8$alkyl, $C_3$-$C_6$alkenyl or $C_3$-$C_6$alkynyl subject to the proviso that the carbon atom attached to the nitrogen atom is primary carbon atom, benzyl, $C_1$-$C_7$acyl or OH-monosubstituted $C_2$-$C_4$alkyl, $R_2$ is hydrogen, $C_1$-$C_4$alkyl or phenyl, $R_3$ is a group of the formula (II)

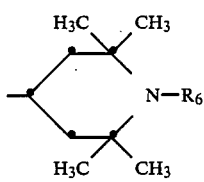

with $R_6$ being as defined for $R_1$, $R_4$ is —COOR$_3$ or —CN and, if n is 1, $R_5$ is hydrogen, $C_1$-$C_{18}$alkyl, $C_2$-$C_4$alkyl substituted by $C_1$-$C_{12}$alkoxy or di($C_1$-$C_6$alkyl)amino, or $C_5$-$C_{12}$cycloalkyl unsubstituted or substituted by 1, 2 or 3 $C_1$-$C_4$alkyl radicals, benzyl or benzyl substituted by 1, 2 or 3 $C_1$-$C_4$alkyl radicals, or a group of the formula (II), and, if n is 1 and $R_4$ is —CN, $R_3$ is additionally a group of the formula

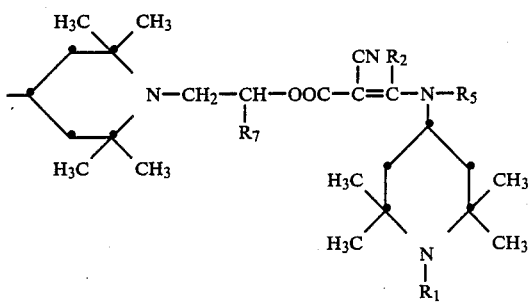

with $R_1$, $R_2$ and $R_5$ being as defined above and $R_7$ being as defined for $R_2$, and, if n is 2, $R_5$ is $C_2$-$C_{12}$alkylene, $C_6$-$C_{15}$cycloalkylene, phenylene, xylylene or $C_4$-$C_{12}$alkylene which is interrupted in the chain by one or two oxygen atoms or one or two groups

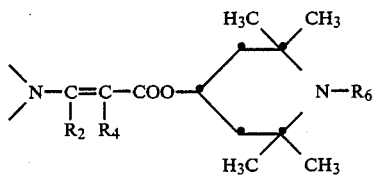

with $R_2$, $R_4$ and $R_6$ being as defined above.

$R_1$ and $R_6$ as $C_1$-$C_8$alkyl are for example methyl, ethyl, propyl, butyl, pentyl, hexyl, heptyl or octyl. $C_1$-$C_4$alkyl, in particular methyl is preferred.

$R_1$ and $R_6$ as $C_3$-$C_6$alkenyl are for example allyl, 2-butenyl or 2-hexenyl. Allyl is preferred.

$R_1$ and $R_6$ as $C_3$-$C_6$alkynyl are preferably propargyl.

$R_1$ and $R_6$ as $C_1$-$C_7$acyl may be benzoyl or an aliphatic $C_1$-$C_7$acyl group, e.g. $C_1$-$C_7$alkanoyl or $C_3$-$C_7$alkenoyl. Examples of an aliphatic acyl group are formyl, acetyl, propionyl, butyryl, caproyl, acryloyl and crotonoyl. Acetyl is preferred.

$R_1$ and $R_6$ as $C_2$-$C_4$alkyl which is monosubstituted by —OH are for example 2-hydroxyethyl, 2-hydroxypropyl, 3-hydroxypropyl or 4-hydroxypropyl. 2-Hydroxyethyl is preferred.

$R_2$ and $R_7$ as $C_1$-$C_4$alkyl are for example methyl, ethyl, propyl, isopropyl, butyl or isobutyl.

$R_5$ as $C_1$-$C_{18}$alkyl is for example methyl, ethyl, propyl, isopropyl, butyl, 2-butyl, isobutyl, t-butyl, pentyl, isopentyl, hexyl, heptyl, octyl, 2-ethylhexyl, nonyl, decyl, undecyl, dodecyl, tridecyl, tetradecyl, hexadecyl or octadecyl. $C_1$-$C_{12}$alkyl, in particular $C_1$-$C_8$alkyl, are preferred. $R_5$ as ethyl or n-butyl is especially preferred.

$R_5$ as $C_2$-$C_4$alkyl which is substituted by $C_1$-$C_{12}$alkoxy is for example 2-methoxyethyl, 2-ethoxyethyl, 3-methoxypropyl, 3-ethoxypropyl, 3-butoxypropyl, 3-octoxypropyl, 4-methoxybutyl or 4-ethoxybutyl. $C_2$-$C_3$alkyl substituted by $C_1$-$C_8$alkoxy is preferred.

$R_5$ as $C_1$-$C_4$alkyl which is substituted by di($C_1$-$C_6$alkyl)amino is for example 2-dimethylaminoethyl, 2-diethylaminoethyl, 3-dimethylaminopropyl, 3-diethylaminopropyl or 3-dibutylaminopropyl. $C_2$-$C_3$alkyl which is substituted by di($C_1$-$C_4$alkyl)amino is preferred.

$R_5$ as $C_5$-$C_{12}$cycloalkyl which may optionally be substituted by 1, 2 or 3 $C_1$-$C_4$alkyl radicals, in particular methyl, is for example cyclopentyl, cyclohexyl, methylcyclohexyl, dimethylcyclohexyl, trimethylcyclohexyl, cyclooctyl or cyclododecyl. $C_5$-$C_8$cycloalkyl, in particular cyclohexyl, unsubstituted or substituted by methyl is preferred.

$R_5$ as benzyl which may be substituted by 1, 2 or 3 $C_1$–$C_4$alkyl radicals is for example methylbenzyl, dimethylbenzyl, trimethylbenzyl or t-butylbenzyl.

$R_5$ as $C_2$–$C_{12}$alkylene is for example ethylene, propylene, trimethylene, tetramethylene, pentamethylene, 2,2-dimethyltrimethylene, hexamethylene, octamethylene, trimethylhexamethylene, decamethylene or dodecamethylene. $C_2$–$C_6$alkylene is preferred.

$R_5$ as $C_6$–$C_{15}$cycloalkylene may be a saturated hydrocarbon group with two free valencies and at least one cyclic unit. Examples of $R_5$ are cyclohexylenedialkylene of 8 to 15 carbon atoms and alkylenedicyclohexylene of 13 to 15 carbon atoms. Cyclohexylenedimethylene and methylenedicyclohexylene are preferred. $R_5$ may also be alkylidenedicyclohexylene of 14 to 15 carbon atoms, in particular isopropylidenedicyclohexylene, or $R_5$ may be cyclohexylene.

$R_5$ as $C_4$–$C_{12}$alkylene which is interrupted in the chain by one or two oxygen atoms is for example 4-oxaheptane-1,7-diyl, 4,7-dioxadecane-1,10-diyl or 4,9-dioxadodecane-1,12-diyl.

Those compounds of the formula (I) are preferred in which n is 1 or 2, $R_1$ and $R_6$, which can be identical or different, are hydrogen, methyl, allyl, benzyl or acetyl, $R_2$ is hydrogen or methyl, $R_4$ is —CN or —COOR$_3$, is a group of the formula (II), and, if n is 1, $R_5$ is hydrogen, $C_1$–$C_{12}$alkyl, $C_2$–$C_3$alkyl substituted by $C_1$–$C_8$alkoxy or di($C_1$–$C_4$alkyl)amino, or cyclohexyl, benzyl or a group of the formula (II), and, if n is 1 and $R_4$ is —CN, $R_3$ is additionally a group of the formula

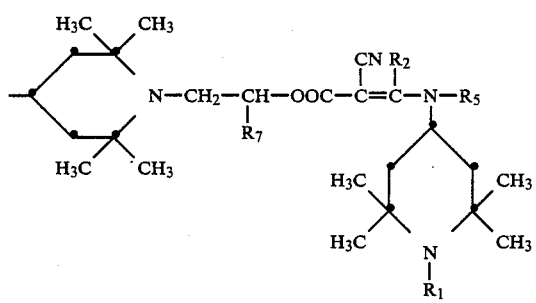

where $R_1$, $R_2$ and $R_5$ are as defined above and $R_7$ is hydrogen or methyl, and, if n is 2, $R_5$ is $C_2$–$C_6$alkylene, $C_6$–$C_{13}$cycloalkylene or $C_6$–$C_{10}$alkylene which is interrupted in the chain by one or two oxygen atoms.

Those compounds of the formula (I) are particularly preferred in which n is 1 or 2, $R_1$ is hydrogen or methyl, $R_2$ is hydrogen, $R_4$ is —CN or —COOR$_3$ with $R_3$ being 2,2,6,6-tetramethyl-4-piperidyl or 1,2,2,6,6-pentamethyl-4-piperidyl, and, if n is 1, $R_5$ is hydrogen, $C_1$–$C_8$alkyl, cyclohexyl, benzyl, 2,2,6,6-tetramethyl-4-piperidyl or 1,2,2,6,6-pentamethyl-4-piperidyl and, if n is 1 and $R_4$ is —CN, $R_3$ is additionally a group of the formula

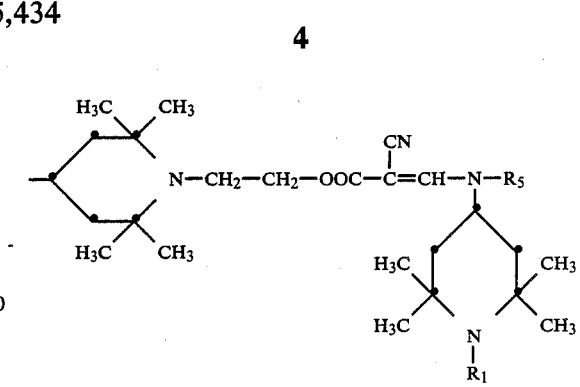

with $R_1$ being hydrogen or methyl and $R_5$ being as defined above, and, if n is 2, $R_5$ is $C_2$–$C_6$alkylene.

Compounds of the formula (I) of particular interest are those in which n is 1 or 2, $R_1$ is hydrogen, $R_2$ is hydrogen, $R_4$ is —CN or —COOR$_3$ with $R_3$ being 2,2,6,6-tetramethyl-4-piperidyl or 1,2,2,6,6-pentamethyl-4-piperidyl, and, if n is 1, $R_5$ is $C_1$–$C_8$alkyl, cyclohexyl, or 2,2,6,6-tetramethyl-4-piperidyl and, if n is 1 and $R_4$ is —CN, $R_3$ is additionally a group of the formula

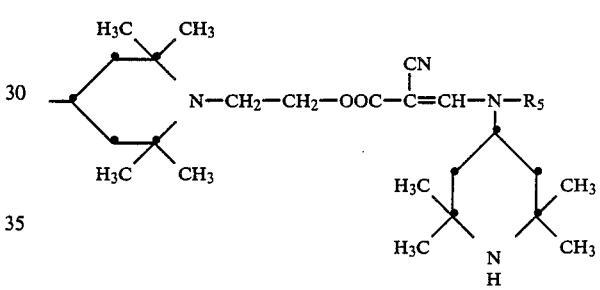

with $R_5$ being as defined above, and, if n is 2, $R_5$ is $C_2$–$C_6$alkylene.

Compounds of the formula (I) of special interest are those in which n is 1 or 2, $R_1$ is hydrogen, $R_2$ is hydrogen, $R_4$ is —N or —COOR$_3$ with $R_3$ being 2,2,6,6-tetramethyl-4-piperidyl or 1,2,2,6,6-pentamethyl-4-piperidyl, and, if n is 1, $R_5$ is $C_1$–$C_4$alkyl and, if n is 1 and $R_4$ is —CN, $R_3$ is additionally a group of the formula

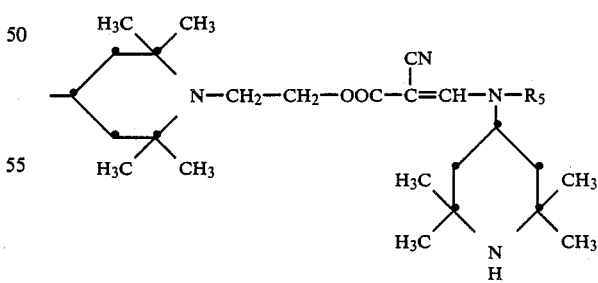

with $R_5$ being $C_1$–$C_4$alkyl, and, if n is 2, $R_5$ is $C_2$–$C_6$alkylene.

$R_1$ and $R_6$ are preferably hydrogen, methyl, allyl, benzyl or acetyl, in particular hydrogen or methyl. n is preferably 1.

The following examples of compounds of the formula (I) are of special interest:

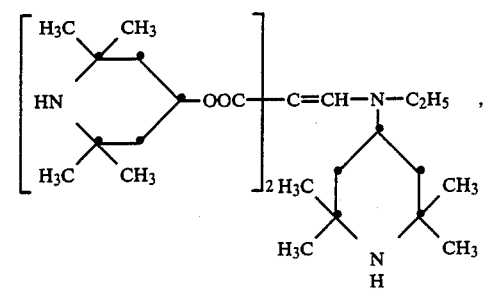

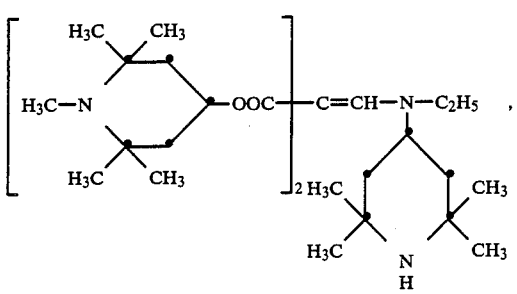

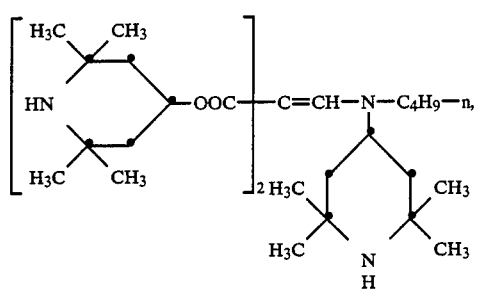

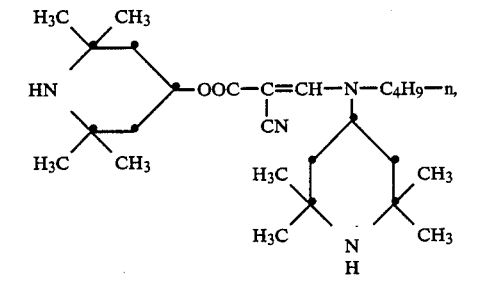

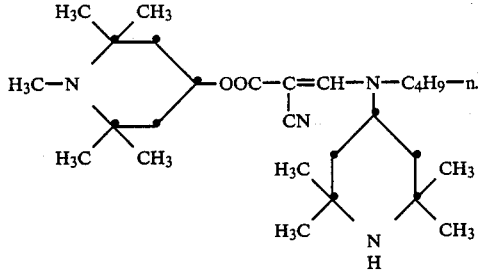

The compounds of the formula (I) can be prepared by processes known per se, e.g. by reacting a compound of the formula (III)

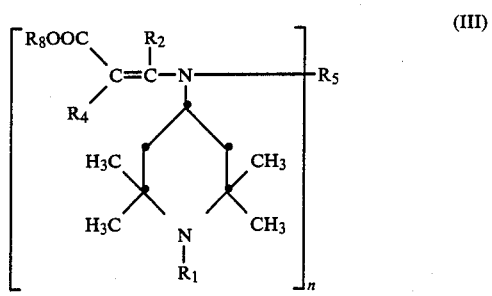

in which n, $R_1$, $R_2$, $R_4$ and $R_5$ are as defined as above and $R_8$ is $C_1$–$C_4$alkyl, with a piperidinole of the formula (IV)

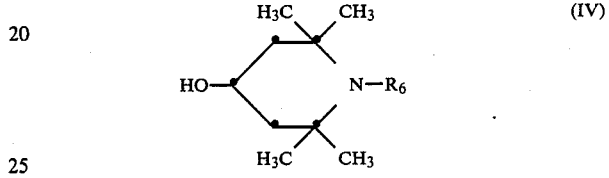

in which $R_6$ is as defined above.

If in the compounds of the formula (I) n is 1, $R_4$ is —CN and $R_3$ is a group of formula

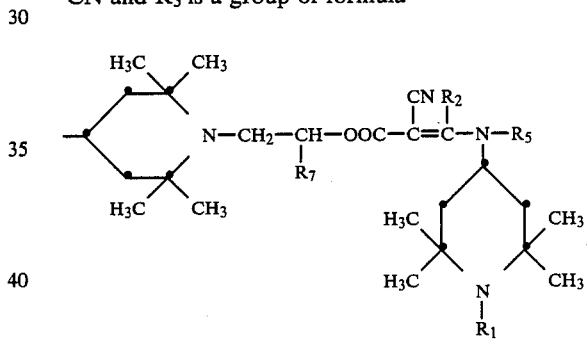

with $R_1$, $R_2$, $R_5$ and $R_7$ being as defined above, said compounds can be prepared by reacting a compound of the formula (III) with a diol of the formula (V)

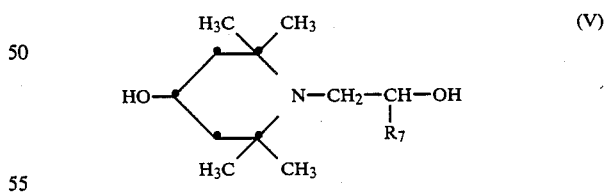

with $R_7$ being as defined above.

The reaction may be carried out for example with or without an inert solvent, in the presence of a transesterification catalyst, e.g. alkali metals, their hydrides, amides or alcoholates, or titanium-IV alkoxides, at a temperature between 100° and 200° C., preferably 120° and 180° C.

The compounds of the formula (III) can be prepared e.g. as described in U.S. Pat. No. 4,140,673, by reacting a compound of the formula (VI) with a compound of the formula (VII)

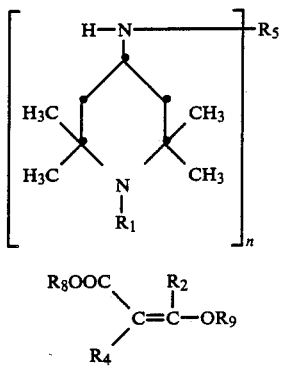 (VI)

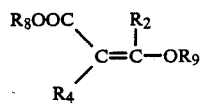 (VII)

in which n, $R_1$, $R_2$, $R_4$, $R_5$ and $R_8$ are as defined above and $R_9$ is methyl or ethyl.

As mentioned at the outset, the compounds of the formula (I) are very effective in improving the light stability, heat stability and oxidation stability of organic materials, in particular synthetic polymers and copolymers. Owing to these characteristics, they can be successfully used as additives in polymer and/or copolymer compositions for use in the production of durable manufactured articles. In the said compositions, which can also contain conventional additives, the compounds of the formula (I) may be added as individual compounds or mixtures of them, in quantities of e.g. 0.10 to 5% by weight and preferably 0.05 to 1% by weight, relative to the organic material to be stabilized.

Therefore, a further object of the invention is a composition comprising an organic material subject to thermal, oxidative and light-induced degradation and at least one compound of the formula (I).

Those compositions are preferred, wherein the organic material is a synthetic polymer, in particular a polyolefin, e.g. polyethylene or polypropylene.

Examples of organic materials which can be stabilized by compounds of the formula (I) are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE).

2. Mixtures of the polyners mentioned under (1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefines and diolefines with each other or with other vinyl monomers, such as, for example, ethylene/propylene, linear low density polyethylene (LLDPE) and its mixtures with low density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene to ethylidene-norbornene; as well as mixtures of such copolymers and their mixtures with polymers mentioned in (1) above, for example polypropylene/ethylene-propylene-copolymers, LDPE/EVA, LDPE/EAA, LLDPE/EVA and LLDPE/EAA.

3a. Hydrocarbon resins (for example $C_5$–$C_9$) and hydrogenated modifications thereof (for example tackyfiers).

4. Polystyrene, poly-(p-methylstyrene), poly-(α-methylstyrene).

5. Copolymers of styrene or α-methylstyrene with dienes or acrylic derivatives, such as, for example, styrene/butadiene, styrene/acrylonitrile, styrene/alkyl methacrylate, styrene/maleic anhydride, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide or polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadien, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine; as well as their copolymers with olefins mentioned in (1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylenediamine and adipic acid; polyamides prepared from hexamethylene diamine and isophthalic or/and terephthalic acid and optionally an elastomer as modifier, for example poly-2,4,4,-trimethylhexamethylene terephthalamide or poly-m-phenylene isophthalamide. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2,-(4-hydroxyphenyl)-propane]terephthalate and polyhydroxybenzoates as well as block-copolyether-esters derived from polyethers having hydroxyl end groups.

18. Polycarbonates and polyester-carbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymerhomologous manner, such as cellulose acetates, cellulose propionates and cellulose butyrates, or the cellulose ethers, such as methylcellulose; rosins and their derivatives.

27. Mixtures of polymers as mentioned above, for example PP/EPDM, Polyamide 6/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

The compounds of the formula (I) can be incorporated into the polymeric materials by various processes, such as dry blending in the form of solutions or suspensions or in the form of a masterbatch; in these operations, the polymer or copolymer can be employed in the form of powder, granules, solutions, suspensions or in the form of a latex.

The polymers stabilized with the products of the formula (I) can be used for the preparation of moulded articles, films, tapes, monofilaments, surface-coatings and the like.

The compounds of the formula (I) are especially useful for stabilizing polypropylene tapes.

If desired, other additives, such as antioxidants, UV absorbers, nickel stabilizers, pigments, fillers, plasticizers, antistatic agents, flameproofing agents, lubricants, anti-corrosion agents and metal deactivators, can be added to the mixtures of the compounds of the formula (I) with the organic material to be stabilized.

Examples of additives which can be mixed with the compounds of the formula (I) are in particular:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'- methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol, 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl)isocyanurate. 1.6. Acylaminophenols, for example 4-hydroxyanilide of lauric acid, 4-hydroxyanilide of stearic acid, 2,4-bis(octylmercapto)-6-(3,5-di-tert-butyl-4-hydroxyanilino)-s-triazine, octyl N-(3,5-di-tert-butyl-4-hydroxyphenyl)carbamate.

1.7. Esters of β-(3,5-di-tert-butyl-4-hydroxyphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.9. Esters of β-(3,5-dicyclohexyl-4-hydroxyphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalic acid diamide.

1.10. Amides of β-(3,5-di-tert-butyl-4-hydroxyphenyl)propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylene-diamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example, 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoneoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane tetracarboxylate, 1,1'-(1,2-ethanediyl)bis(3,3,5,5-tetramethylpiperazinone).

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic acid dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl)4,4'-biphenylene diphosphonite, 3,9-bis(2,4-di-tert-butylphenoxy)-2,4,8,10-tetraoxa-3,9-diphosphaspiro[5.5]undecane.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

The compounds of the formula (III) which are conveniently used in the preparation of the present compounds can be prepared e.g. by analogy to the method described below.

Preparation of ethyl α-ethoxycarbonyl-β-[N-ethyl-N-(2,2,6,6-tetramethyl-4-piperidyl)]-aminoacrylate (compound No. 1)

86.49 g (0.4 mol) of ethyl α-ethoxycarbonyl-β-ethoxyacrylate are slowly added with stirring to 75.24 g (0.4 mol) of 4-ethylamino-2,2,6,6-tetramethylpiperidine, while maintaining ambient temperature.

After 8 hours at this temperature, a thick yellow clear oil is obtained which is purified by distillation; boiling point = 164° C./2.66 mbar.

Analysis for $C_{19}H_{34}N_2O_4$: Calculated: C 64.38%; H 9.67%; N 7.90%. Found: C 64.28%; H 9.68%; N 7.87%.

Proceeding in analogous manner, the following compounds of the formula

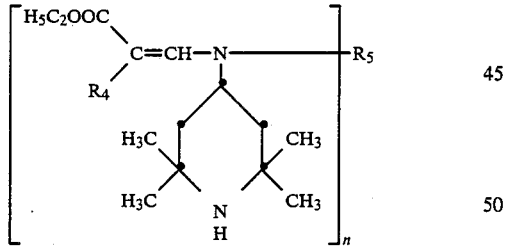

with n, $R_4$ and $R_5$ being as defined in the table 1 are prepared.

TABLE 1

| Compound No. | n | $R_4$ | $R_5$ | Melting point (°C.) |
| --- | --- | --- | --- | --- |
| 2 | 1 | —COOC$_2$H$_5$ | —H | 51–53 |
| 3 | 1 | —COOC$_2$H$_5$ | —C$_4$H$_9$-n | 52–53 |
| 4 | 1 | —CN | —C$_2$H$_5$ | 100–102 |
| 5 | 1 | —CN | —C$_4$H$_9$-n | 93–94 |
| 6 | 2 | —CN | —(CH$_2$)$_2$— | 193–194 |
| 7 | 2 | —CN | —(CH$_2$)$_6$— | 165–166 |

EXAMPLE 1

Preparation of 2,2,6,6-tetramethyl-4-piperidyl α-(2,2,6,6-tetramethyl-4-piperidyloxycarbonyl)-β-[N-ethyl-N-(2,2,6,6-tetramethyl-4-piperidyl)]-aminoacrylate 49.63 g (0.14 mol) of ethyl α-ethoxycarbonyl-β-[N-ethyl-N-(2,2,6,6-tetramethyl-4-piperidyl)]-aminoacrylate (compound No. 1), 45.64 g (0.29 mol) of 2,2,6,6-tetramethyl-4-piperidinol and 200 ml of xylene are heated under reflux for 2 hours, any traces of humidity present in the reagents being removed azeotropically.

1.5 g of sodium methylate are added, and the mixture is heated under reflux for 8 hours, the ethanol set free in the reaction being removed azeotropically.

The mixture is then cooled, washed with water, dried over sodium sulfate, filtered and evaporated in vacuo (23 mbar).

The residue obtained is crystallized from n-hexane, a product of melting point = 138°–139° C. being obtained.

Analysis for $C_{33}H_{60}N_4O_4$: Calculated: C 68.71%; H 10.48%; N 9.71%. Found: C 68.40%; H 10.42%; N 9.71%.

EXAMPLES 2–9

Following the procedure described in Example 1 and using the appropriate intermediates, the following compounds are prepared:

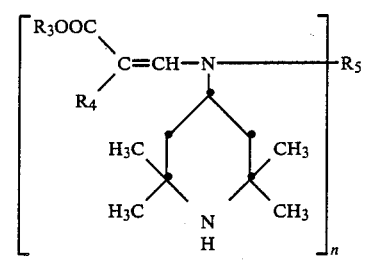

TABLE 2

| Example No. | n | $R_3$ | $R_4$ | $R_5$ | Melting point (°C.) |
| --- | --- | --- | --- | --- | --- |
| 2 | 1 | H₃C—⟨NH⟩—CH₃ (2,2,6,6-tetramethylpiperidinyl) | —COO—⟨NH⟩— (2,2,6,6-tetramethylpiperidinyl) | —H | 188–190 |

TABLE 2-continued

| Example No. | n | R₃ | R₄ | R₅ | Melting point (°C.) |
|---|---|---|---|---|---|
| 3 | 1 | 1,2,2,6,6-pentamethyl-4-piperidinyl | —COO—(1,2,2,6,6-pentamethyl-4-piperidinyl)— | —C₂H₅ | 160–161 |
| 4 | 1 | 2,2,6,6-tetramethyl-4-piperidinyl | —COO—(2,2,6,6-tetramethyl-4-piperidinyl)— | —C₄H₉—n | 136–137 |
| 5 | 1 | 2,2,6,6-tetramethyl-4-piperidinyl | —CN | —C₄H₉—n | 118–119 |
| 6 | 1 | 1,2,2,6,6-pentamethyl-4-piperidinyl | —CN | —C₄H₉—n | 130–131 |
| 7 | 1 | (*) | —CN | —C₂H₅ | 193–194 |
| 8 | 2 | 2,2,6,6-tetramethyl-4-piperidinyl | —CN | —(CH₂)₂— | 272–273 |
| 9 | 2 | 2,2,6,6-tetramethyl-4-piperidinyl | —CN | —(CH₂)₆— | 246–248 |

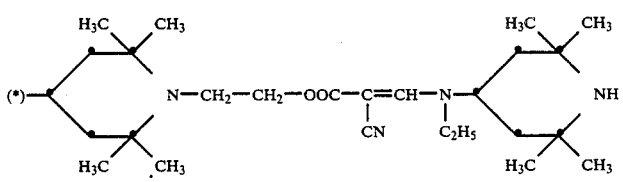

(*) = (1,2,2,6,6-pentamethyl-4-piperidinyl)—N—CH₂—CH₂—OOC—C(CN)=CH—N(C₂H₅)—(2,2,6,6-tetramethyl-4-piperidinyl)

EXAMPLE 10

Stabilization of polypropylene tapes 1 g of each of the compounds indicated in Table 3, 0.5 g of tris-(2,4-di-t-butylphenyl) phosphite, 0.5 g of pentaerythritol tetrakis-[3-(3′,5′-di-t-butyl-4-hydroxyphenyl)-propionate] and 1 g of calcium stearate are mixed in a slow mixer with 1000 g of polypropylene powder of melt index=3 g/10 minutes (measured at 230° C. and 2.16 kg). The mixtures are extruded at 200°–220° C. to give polymer granules which are then converted into stretched tapes of 50 μm thickness and 2.5 mm width, using a pilot type apparatus (Leonard-Sumirago (VA) Italy) under the following working conditions:

extruder temperature: 210°–230° C.
head temperature: 240°–260° C.
stretch ratio: 1:6

The tapes thus prepared are exposed, mounted on a white card, in a Model 65WR Weather-O-Meter (ASTM G 26-77), with a black panel temperature of 63° C.

The residual tenacity is measured on samples, taken after various times of exposure to light, by means of a constant-speed tensometer; the exposure time in hours ($T_{50}$) needed to halve the initial tenacity is then calculated.

The results obtained are shown in Table 3:

TABLE 3

| Stabilizer | $T_{50}$ (hours) |
| --- | --- |
| Without stabilizer | 430 |
| Compound from Example 1 | 4,450 |
| Compound from Example 3 | 3,900 |
| Compound from Example 4 | 3,800 |
| Compound from Example 5 | 3,400 |
| Compound from Example 6 | 3,700 |
| Compound from Example 9 | 3,100 |

What is claimed is:

1. A piperidine compound of the formula (I)

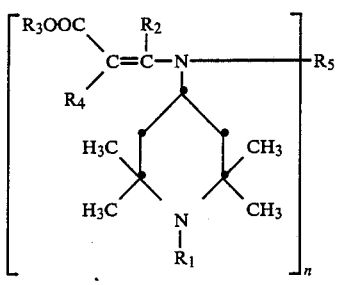

(I)

in which n is 1 or 2, $R_1$ is hydrogen, O°, NO, cyanomethyl, $C_1$–$C_8$-alkyl, $C_3$–$C_6$alkenyl or $C_3$–$C_6$alkynyl subject to the proviso that the carbon atom attached to the nitrogen atom is a primary carbon atom, benzyl, $C_1$–$C_7$acyl or OH-monosubstituted $C_2$–$C_4$alkyl, $R_2$ is hydrogen, $C_1$–$C_4$alkyl or phenyl, $R_3$ is a group of the formula (II)

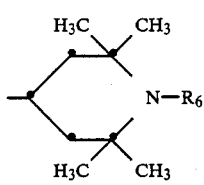

(II)

with $R_6$ being as defined for $R_1$, $R_4$ is —COOR$_3$ or —CN and, if n is 1, $R_5$ is hydrogen, $C_1$–$C_{18}$alkyl, $C_2$–$C_4$alkyl substituted by $C_1$–$C_{12}$alkoxy or di($C_1$–$C_6$alkyl)amino, or $C_5$–$C_{12}$cycloalkyl unsubstituted or substituted by 1, 2 or 3 $C_1$–$C_4$alkyl radicals, benzyl, benzyl substituted by 1, 2 or 3 $C_1$–$C_4$alkyl radicals, or a group of the formula (II), and, if n is 1 and $R_4$ is —CN, $R_3$ is additionally a group of the formula

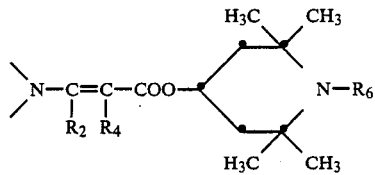

with $R_1$, $R_2$ and $R_5$ being as defined above and $R_7$ being as defined for $R_2$, and, if n is 2, $R_5$ is $C_2$–$C_{12}$alkylene, $C_6$–$C_{15}$cycloalkylene, phenylene, xylylene or $C_4$–$C_{12}$alkylene which is interrupted in the chain by one or two oxygen atoms or one or two groups

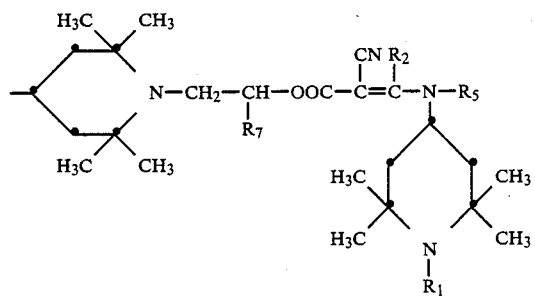

with $R_2$, $R_4$ and $R_6$ being as defined above.

2. A compound of the formula (I) according to claim 1, wherein n is 1 or 2, $R_1$ and $R_6$, which are identical or different, are hydrogen, methyl, allyl, benzyl or acetyl, $R_2$ is hydrogen or methyl, $R_4$ is —CN or —COOR$_3$, where $R_3$ is a group of the formula (II), and, if n is 1, $R_5$ is hydrogen, $C_1$–$C_{12}$alkyl, $C_2$–$C_3$alkyl substituted by $C_1$–$C_8$alkoxy or di($C_1$–$C_4$alkyl)amino, or cyclohexyl, benzyl or a group of the formula (II), and, if n is 1 and $R_4$ is —CN, $R_3$ is additionally a group of the formula

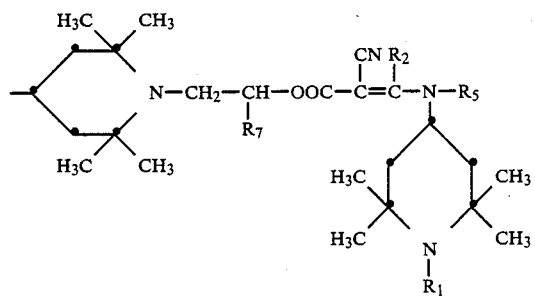

where $R_1$, $R_2$ and $R_5$ are as defined above and $R_7$ is hydrogen or methyl, and, if n is 2, $R_5$ is $C_2$–$C_6$alkylene, $C_6$–$C_{13}$cycloalkylene or $C_6$–$C_{10}$alkylene which is interrupted in the chain by one or two oxygen atoms.

3. A compound of the formula (I) according to claim 1, wherein n is 1 or 2, $R_1$ is hydrogen or methyl, $R_2$ is hydrogen, $R_4$ is —CN or —COOR$_3$ with $R_3$ being 2,2,6,6-tetramethyl-4-piperidyl or 1,2,2,6,6-pentamethyl-4-piperidyl, and, if n is 1, $R_5$ is hydrogen, $C_1$–$C_8$alkyl, cyclohexyl, benzyl, 2,2,6,6-tetramethyl-4-piperidyl or 1,2,2,6,6-pentamethyl-4-piperidyl, and, if n is 1 and $R_4$ is —CN, $R_3$ is additionally a group of the formula

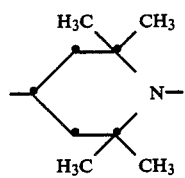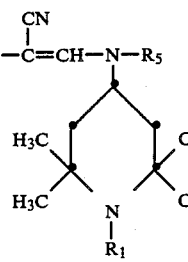

with R₁ being hydrogen or methyl and R₅ being as defined above, and, if n is 2, R₅ is $C_2$-$C_6$alkylene.

4. A compound of the formula (I) according to claim 1, wherein n is 1 or 2, R₁ is hydrogen, R₂ is hydrogen, R₄ is —CN or —COOR₃ with R₃ being 2,2,6,6-tetramethyl-4-piperidyl or 1,2,2,6,6-pentamethyl-4-piperidyl, and, if n is 1, R₅ is $C_1$-$C_8$alkyl, cyclohexyl or 2,2,6,6-tetramethyl-4-piperidyl, and, if n is 1 and R₄ is —CN, R₃ is additionally a group of the formula

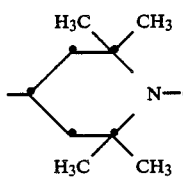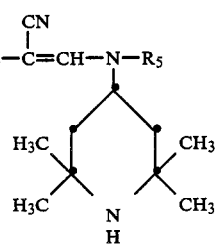

with R₅ being as defined above, and, if n is 2, R₅ is $C_2$-$C_6$alkylene.

5. A compound of the formula (I) according to claim 1, wherein n is 1 or 2, R₁ is hydrogen, R₂ is hydrogen, R₄ is —CN or —COOR₃ with R₃ being 2,2,6,6-tetramethyl-4-piperidyl or 1,2,2,6,6-pentamethyl-4-piperidyl, and, if n is 1, R₅ is $C_1$-$C_4$alkyl and, if n is 1 and R₄ is —CN, R₃ is additionally a group of the formula

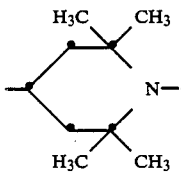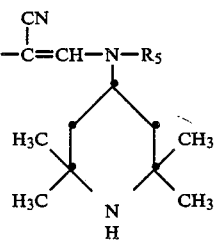

with R₅ being $C_1$-$C_4$alkyl, and, if n is 2, R₅ is $C_2$-$C_6$alkylene.

6. A compound of the formula (I) according to claim 1, wherein R₁ and R₆ independently of one another are hydrogen, methyl, allyl, benzyl or acetyl.

7. A compound of the formula (I) according to claim 1, wherein n is 1.

8. A compound of the formula

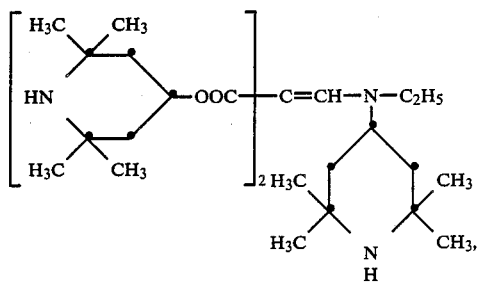

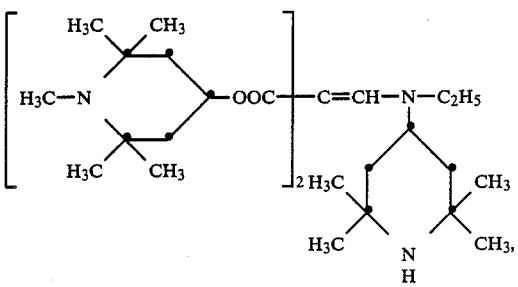

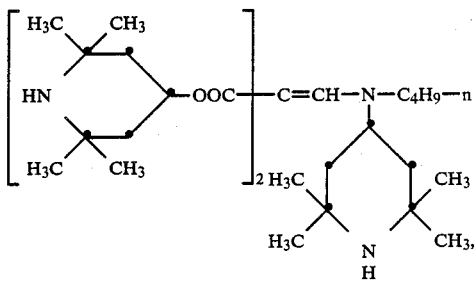

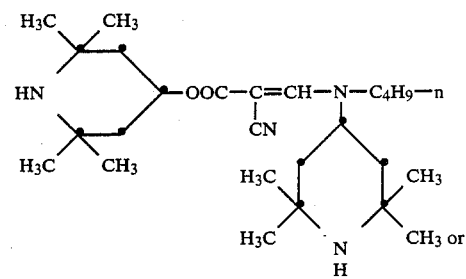

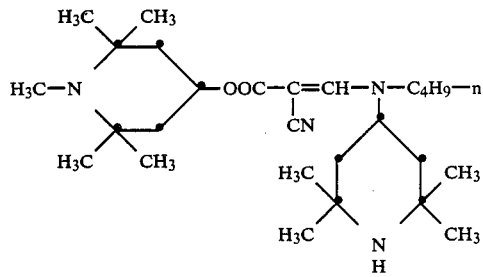

according to claim 1.

* * * * *